United States Patent [19]
Sittinger et al.

[11] Patent Number: 5,891,455
[45] Date of Patent: Apr. 6, 1999

[54] PROCESS FOR PRODUCING AN IMPLANT FROM CELL CULTURES

[76] Inventors: Michael Sittinger, Alt-Buckow 42c, D-12349 Berlin; Jesus Bujia, Dreyerstrasse 6, D-80689 Munich, both of Germany

[21] Appl. No.: 513,995

[22] PCT Filed: Mar. 3, 1994

[86] PCT No.: PCT/DE94/00235

§ 371 Date: Sep. 6, 1996

§ 102(e) Date: Sep. 6, 1996

[87] PCT Pub. No.: WO94/20151

PCT Pub. Date: Sep. 15, 1994

[30] Foreign Application Priority Data

Mar. 3, 1993 [DE] Germany ............... 43 06 661.5

[51] Int. Cl.$^6$ ............... A61F 2/00; C12N 5/00; C12N 5/02
[52] U.S. Cl. ............... 424/426; 424/422; 424/423; 424/424; 435/325; 435/366; 435/382
[58] Field of Search ............... 424/9.1, 9.2, 9.23, 424/93.1, 93.7, 408, 422, 423, 426, 451, 452, 424; 435/325, 382, 366; 427/2.1, 2.14, 2.24, 207.1

[56] References Cited

FOREIGN PATENT DOCUMENTS

WO 88/03785 6/1988 WIPO .
WO 91/01720 2/1991 WIPO ............... 424/93.1

OTHER PUBLICATIONS

Cima et al. Tissue engineering by cell transplantation using degradable polymer substrates. J. of Biomechanical Engineering, vol. 113, pp. 143–151., May 1991.

*Primary Examiner*—Deborah Crouch
*Assistant Examiner*—Deborah J. R. Clark
*Attorney, Agent, or Firm*—Blank Rome Comisky & McCauley LLP

[57] ABSTRACT

In a process for producing an implant from cell cultures in vitro, tissue cells, particularly cartilage cells, are introduced into a three-dimensional self-supporting structure preformed preferably from nonwoven polymer material, the supporting structure having a shape corresponding to that of the desired implant. The supporting structure is then perfused with a nourishing solution for a sufficiently long period of time that an intercellular matrix which bonds the cells together is formed at least partially within the supporting structure. The supporting structure with the at least partially formed intercellular matrix may then be implanted. Upon subsequent resorption of the supporting structure, the shape of the implant is maintained and preserved by the intercellular matrix then formed.

17 Claims, 1 Drawing Sheet

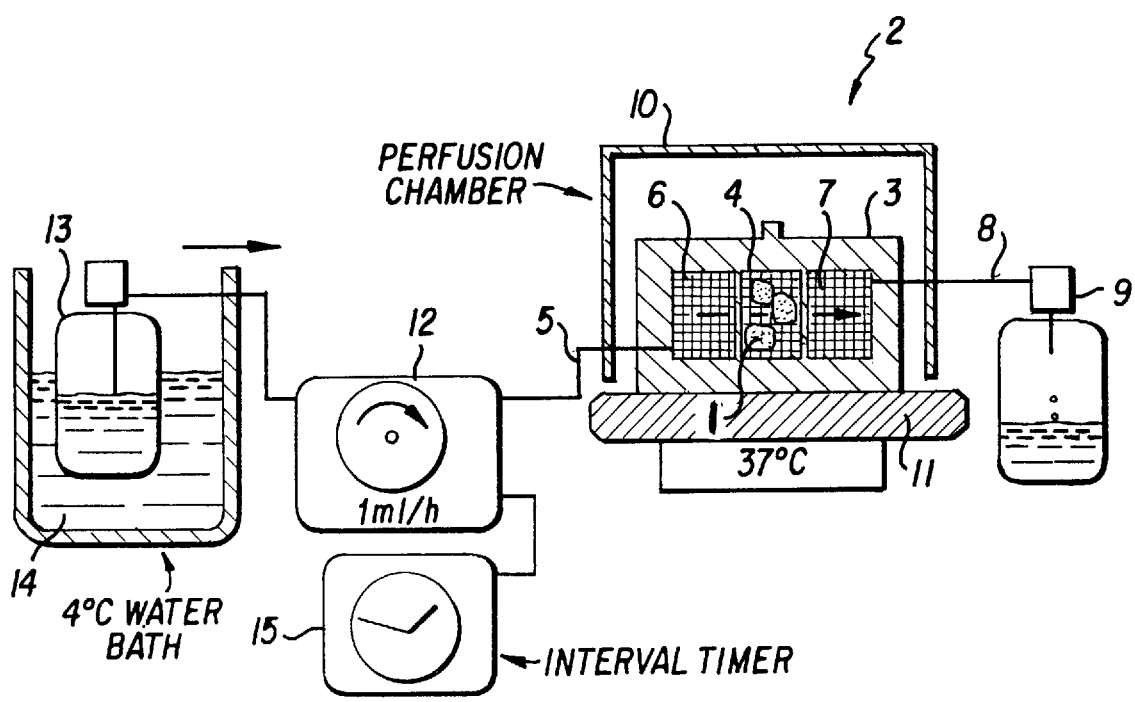

PROCESS FOR PRODUCING AN IMPLANT FROM CELL CULTURES

CROSS-REFERENCE TO RELATED APPLICATION

This application is based on International Patent Application No. PCT/DE94/00235, filed Mar. 3, 1994, from application No. P 4306661.5, filed in Germany on Mar. 3, 1993, for which applicant claims priority under 35 U.S. C. 119(b).

BACKGROUND OF THE INVENTION

The invention relates to a method for the production of an implant from cell cultures, particularly an implant of cartilage cells whereby these cells are applied to an absorbable support structure and then implanted.

Should the body's own tissue be removed, so that cartilage, for example, must be replaced, two options are presently available. One option is that the required tissue may be taken from cadavers, preserved, and then implanted. In this case, immune reactions sometimes occur. The other option is to replace the removed tissue by implanting tissue taken from locations of the patient's own body which are not externally visible. Here, no risk of immune reactions is present.

A serious disadvantage of these two methods, however, is that an adequate amount of replacement tissue may not be available, so that the desired substitution of tissue cannot be completed.

Therefore, a third method has been proposed. In this method, cells which have been isolated and propagated in a conventional manner are applied to a polymer fiber bundle of absorbable material, and the bundle is implanted. See C. A. Vacanti et al., *Plastic and Reconstructive Surgery* 8 (5) 753–759, November 1991. By layering the bundle with superimposed and adjacent layers, the implant can be shaped somewhat in a three-dimensional manner. After implantation, the polymer material is absorbed, whereby simultaneously the intercellular matrix between the individual cells is formed from collagen, especially so that in the final stage a tissue structure results which is integrated into the surrounding tissue and is fully functional.

This third method is still in the trial stage with tests being conducted on animals, but has not yet been applied in human medicine.

Difficulties probably arise with this method in the shaping of the desired implant, because during the absorption of the fiber material, shape stability cannot be expected from the layers superimposed and adjacent to one another. Furthermore, for larger implants, difficulties result with the nourishment of the individual cells which lie inside the implant.

SUMMARY OF THE INVENTION

An objective of the present invention is to specify a method by which cell tissue, particularly cartilage, is made available in a configuration which is favorable for implantation. In particular, the implant should be easily molded and maintain its shape in the implanted state and assure secure nourishment of the individual cells in the implant.

This objective is achieved by a method according to the invention for production of an implant from cell cultures, particularly cartilage cells, in which the cells are applied to an absorbable support structure and are subsequently to be implanted together with it, characterized in that a three-dimensional, preformed support structure is fashioned, having a stable shape and corresponding to the desired form of the implant, with an interior cavity, from a material having a cohesive inner surface and low volume such as a nonwoven polymeric material, for example; cells are introduced into the interior cavity of the support structure; and the support structure containing the cells is perfused with a nutrient solution such that the nutrient solution flows through the support structure until an intercellular matrix which binds the cells together has at least partially formed, thereby constituting the specified implant with a stable three-dimensional support structure having the desired shape.

The fundamental concept of the invention resides in the preforming of the three-dimensional support structure with a stable shape suited to the location in which it is to be implanted, and which maintains its shape in the implanted state. The material from which it is formed, such as nonwoven polymeric material, enables a hollow, low volume support structure, e.g., a capsule, to be produced, with a cohesive inner surface of its interior cavity, into which the cells are introduced and a nutrient solution is caused to flow.

The three-dimensional support structure assures that even during absorption the cells maintain a stable shape with their intercellular matrix, and the desired shape of the implant is retained even after implantation.

Perfusion assures that even the cells which lie inside the support structure are sufficiently supplied with nutrient solution, and that this supply is maintained when the intercellular matrix has at least partially formed. Through the construction of the support structure and an optional appropriate preparation, the entry of the nutrient solution into and to permeate the support structure essentially occurs only by diffusion, which corresponds to the situation in vivo. Such cellular nourishment can also be assured by encasing the total support structure with a material that only allows diffusion, such as agarose, for example.

This nourishment of the cells in the support structure by means of diffusion prevents the cell products, particularly those collagens and proteoglycans which are required for the construction of the intercellular matrix, from flowing out of the cell association. The retention of these necessary factors can be further improved and supported by performing perfusion of the support structure with nutrient solution at intervals. During pauses in the perfusion, the cell products can be held in place and form compounds with the cells, whereas in the perfusion phases undesirable cell products may also flow out of the support structure and the matrix.

The support structure is biocompatible, preferably a nonwoven material of polymer fibers, particularly polyglycols or polylactides, and is provided with adhesion factors, particularly poly-L-lysine, before the cells are introduced into it. The adhesion factors may be applied by lyophilization to an inner surface of the support structure. Further, the inner cavity or interior cavity of the support structure is designed and dimensioned so that the nutrient solution diffuses through the support structure, and as pointed out above, this diffusion is supported by encasing the support structure with a material such as agarose. It is also preferable that the support structure with the cells it holds be set into a perfusion chamber and intermittently perfused, so that a perfusion phase is followed in each case by a pause. A substance which increases viscosity, preferably agarose, may be added to the suspension of the cells with the culture medium introduced into the support structure. The formation of cells and of an intercellular matrix is supported by adding a morphogenic tissue factor to the support structure, and this morphogenic tissue factor is preferably coupled to an antibody which complexes with the material of the support structure, preferably to haptens which are applied there.

BRIEF DESCRIPTION OF THE DRAWING

FIG. 1-A schematic presentation of the method with regard to the exemplary equipment used in its performance.

DETAILED DESCRIPTION OF THE PREFERRED EMBODIMENT

As pointed out in the summary, the method of the invention is directed to producing an implant with initial support structure of easily molded configuration which has a stable, preformed, three-dimensional, hollow shape conforming to that desired for the environment in which it is to be used, and which maintains its shape in the implanted state despite substantially complete absorption (resorption) of the support structure by virtue of an intercellular matrix that binds together the tissue cells which were introduced into its interior cavity, and that is adapted to facilitate secure nourishment of the cells. The essence of the invention resides in the provision of an implant having these features, and, although an exemplary method will be specified, it will be understood that in doing so any alternative conventional techniques may be employed in the various steps of the method to arrive at the implementation of such an implant. Also, although the description will make specific reference only to the production of cartilage in vitro, it will be further understood that other body tissue may alternatively be produced for purposes of the implant of the invention.

A support structure that will permit stable shaping of the implant is produced from an absorbable (biosorbable), nonwoven polymeric fiber material, suitable examples of which include polyglycols or polylactides. Such materials are readily preformed as by molding to provide a self-supporting structure of predetermined stable shape desired for the implant, with a hollow configuration of minimal material volume (i.e., relatively thin-walled) and an interior cavity having a relatively large cohesive inner surface. This cohesive inner surface is coated or wetted with an adhesion factor, such as poly-L-lysine, for example. An exemplary technique of wetting is to immerse the support structure in a polylisine solution, followed by lyophilization, i.e., freeze-drying, so that the adhesion factor essentially covers the entire inner surface of the support structure.

Cartilage cells from the patient(s) (i.e., cells which are homogeneic to the recipient patient) are propagated in a culture medium in a conventional manner for implantation. When a sufficient number of cells is present in the cell culture, the cells in suspension with the culture medium are introduced into the interior cavity of the three-dimensional support structure. To increase the viscosity of the suspension, an absorbable material suitable for that purpose, such as agarose, may be added to the suspension.

The support structure which holds the cells is then encased with agarose, for example, by immersion into a 2% agarose solution. Thereafter, the support structure is subjected to cold shock, by immersion in a cold water bath of approximately 4° C., for example, to solidify the encasing agarose and also the agarose which is optionally added to the suspension, and thereby facilitate subsequent handling of the implant.

Referring now to the sole Figure of drawing, the support structure(s) 1 prepared in this way is set into perfusion apparatus 2, specifically into perfusion chamber 4 of housing 3 of the apparatus. A nutrient solution is introduced through a supply line 5 into housing 3. The nutrient solution first enters a mixing chamber 6 in which the flow is regulated, before it enters the perfusion chamber 4. An effluent chamber 7 connects with perfusion chamber 4, from which effluent line 8 leads to a receiving container 9. Housing 3 is covered with a covering 10 and is maintained at a constant temperature of 37° C., corresponding to the average body temperature, by heating system 11. Agarose may also be added to perfusion chamber 4.

The nutrient solution, such as that commercially available under the name Hamis F12, is slowly directed through the perfusion chamber 4 by transport through a pump 12, such as a peristaltic pump, mounted in supply line 5 which draws the nutrient solution from a reserve container 13. The latter is located in a water bath 14 held at a temperature of 4° C., for example. The quantity of the nutrient solution pumped into the perfusion chamber 4 through pump 12 is very slight, and, in the case of cartilage production, for example, is adjusted to a flow of approximately one milliliter per hour. In this way, plural support structures—in the drawing, three are shown in perfusion chamber 4 by way of example—can be sufficiently nourished, and these support structures have a cross section in this case of, at most, the size of a thumbnail.

Peristaltic pump 12 is controlled by an interval timer 15 so that the intervals of the perfusion phase can be adjusted depending on the size of the support structure(s) and the perfusion chamber. In practice, the pump and pause intervals are in the range of minutes or hours. Good results have been achieved with pump and pause intervals of approximately 30 minutes each.

The perfusion apparatus is entirely conventional. Such apparatuses serve to culture cells which are applied to a membrane under continuous conditions, as replacement for conventional Petri dishes. Membranes with applied cell cultures are may be introduced into the perfusion chamber through slots.

The nutrient solution directed through perfusion apparatus 2 diffuses through the encasing agarose into support structure 1, so that the cells within the support structure are nourished. By appropriately adjusting the flow of nutrient solution and the interval control for perfusion, the cell products necessary for construction of the intercellular matrix can be made to remain in place, i.e., are retained in the chamber, rather than flow out. Over time, the intercellular matrix with its collagen fibers forms between cells, so that the cells are bound to one another. The support structure and agarose may partially dissolve during this long-term process, but through the construction of the intercellular matrix the predetermined form of the support structure remains so that the desired shape of the implant which is formed thereby is also maintained.

When the intercellular matrix is sufficiently formed, typically from about 10 days to several weeks after initiating the process, the support structure with intercellular matrix binding together the cells may be removed from the perfusion chamber and implanted. In time, the matrix is further formed, while the support structure is absorbed.

The method enables construction of the intercellular matrix in such form in vitro, which had not previously been accomplished. Further, so-called morphogenic tissue factors may be added to the nonwoven material of the support structure to stimulate cell formation and formation of the intercellular matrix, whereby to form cartilage. These factors may be introduced into the support structure either during formation of the intercellular matrix in the perfusion chamber or after the support structure is implanted. One solution consists of coupling the morphogenic tissue factor directly with the nonwoven material of the support structure, or coupling an antibody and providing the nonwoven material with haptens to which the antibodies complex, so that the morphogenic tissue factors have only a local effect in the area of the support structure.

The foregoing disclosure of a presently preferred embodiment is not intended to be limiting, except to the extent of the appended claims.

We claim:

1. A method for producing an implant, said method comprising the sequentially-followed steps of:

producing a hollow capsule from a biosorbable polymer, such that the capsule with an inner cavity constituting the hollow therein forms a shape desired for the implant, wherein said biosorbable polymer is selected to permit passage of nutrient solution thereinto;

introducing cells which are homogeneic to a recipient patient which forms an intercellular matrix into the inner cavity of the implant, such that the cells fill and are enclosed within the cavity;

encasing the capsule with agarose; and perfusing a nutrient solution through the capsule in vitro until an intercellular matrix forms in the inner cavity of the capsule.

2. The method of claim 1, including the step of selecting as the biosorbable polymer a material which retains the shape in which it is formed with stability, including after implantation until it is substantially absorbed.

3. The method of claim 2, wherein said step of perfusing is carried out by placing said encased capsule in a perfusion chamber for a period of time, at a temperature, and at a flow rate and concentration of the nutrient solution to enable said intercellular matrix to form sufficiently to bind the cells together such that the shape of the capsule will be retained by the cells bound in the intercellular matrix after absorption of the encased capsule as an implant.

4. The method of claim 3, wherein during said perfusing step the flow of nutrient solution through the chamber is periodically halted to replenish cell products and formation of compounds thereby with the cells during the pauses.

5. The method of claim 1, wherein the cells introduced into the cavity are obtained from selected tissue of the patient and propagated in a culture medium to form a suspension of propagated cells and culture medium for introduction into said cavity, and further including the step of adding an absorbable material to the suspension to increase the viscosity thereof before introduction into the cavity.

6. The method of claim 5, wherein said added absorbable material is agarose.

7. The method of claim 2, wherein the biosorbable polymer material is further selected to provide a cohesive inner surface of said cavity, and wherein, prior to the step of introducing the cells into the cavity, the cohesive inner surface of the cavity is wetted with an adhesion factor to promote adhesion of the introduced cells thereto.

8. The method of claim 7, wherein the step of wetting the inner surface of the cavity is performed by immersing the capsule in a polylysine solution bath, and removal from the bath followed by freeze-drying the capsule, to promote coverage of the inner surface of the cavity by the adhesion factor.

9. A process for producing an implant, said process comprising the sequential steps of:

pre-forming a three-dimensional, hollow, thin-walled, self-supporting structure with an inner cavity having a large cohesive inner surface and a predetermined stable shape, from a biosorbably biocompatible material selected to permit passage of a nutrient solution thereinto;

introducing a suspension of tissue cells, which form an intercellular matrix and are homogeneic to a recipient patient, in a culture medium in which the cells have been propagated, into the cavity of the supporting structure, to fill and take the shape of the cavity, so that the cellular suspension is enclosed by said inner surface of the cavity; and perfusing a nutrient solution through the supporting structure and cellular suspension therein in vitro until an intercellular matrix forms in the cavity to bind the cells therein together so that the combined intercellular matrix with cells bound therein will maintain the desired shape of the implant despite absorption of the supporting structure.

10. The process of claim 9, wherein said biosorbable biocompatible material is a nonwoven polymeric fiber material.

11. The process of claim 10, wherein said nonwoven polymeric fiber material is selected from the group consisting of polyglycols and polylactides.

12. The process of claim 11, wherein at least said inner surface of the cavity is coated with an adhesion factor before introducing the cellular suspension therein.

13. The process of claim 9, wherein a biocompatible substance is added to the cellular suspension to increase the viscosity thereof.

14. The process of claim 9, wherein the perfusion is carried out by placing the supporting structure containing the cellular suspension in a perfusion chamber for a period of time, at a temperature, and at a flow rate and concentration of the nutrient solution to enable said formation of the intercellular matrix.

15. The process of claim 14, wherein said perfusion of nutrient solution through the chamber is carried out in repeated intervals of perfusion, separated by pause.

16. The process of claim 9, further including encasing the supporting structure containing the cellular suspension in a material that promotes diffusion of the nutrient solution into the supporting structure to nourish the cells therein, before carrying out the step of perfusion.

17. An implant comprising a pre-formed three-dimensional, hollow, thin-walled, self-supporting structure of biosorbable biocompatible material with an inner cavity having a large cohesive inner surface and a predetermined stable shape desired for the implant, and intercellular matrix-forming tissue cells homogeneic to a recipient patient bound in an intercellular matrix filling and enclosed by said cavity, so as to maintain said predetermined stable shape despite absorption of the supporting structure when implanted.

* * * * *